United States Patent [19]

Lai et al.

[11] Patent Number: 5,321,159
[45] Date of Patent: Jun. 14, 1994

[54] DECOLORIZATION OF ALKYLATED DIARYLAMINES

[75] Inventors: John T. Lai; Chong-Kuang Shaw, both of Broadview Heights; Deborah S. Filla, Twinsburg, all of Ohio

[73] Assignee: The B. F. Goodrich Company, Akron, Ohio

[21] Appl. No.: 161,910

[22] Filed: Dec. 8, 1993

Related U.S. Application Data

[63] Continuation-in-part of Ser. No. 993,924, Dec. 18, 1992, abandoned.

[51] Int. Cl.$^5$ .......................................... C07C 209/84
[52] U.S. Cl. ...................................... 564/437; 564/433
[58] Field of Search .............................. 564/433, 437

[56] References Cited

U.S. PATENT DOCUMENTS

| | | | |
|---|---|---|---|
| 3,492,233 | 1/1970 | Hepplewhite et al. | 252/51.5 |
| 3,509,214 | 4/1970 | Braid | 260/576 |
| 3,539,539 | 11/1970 | Goetzke | 260/78 |
| 3,573,206 | 3/1971 | Braid et al. | 252/51.5 |
| 3,634,248 | 1/1972 | Andress, et al. | 252/51.5 |
| 3,655,559 | 4/1992 | Holt | 252/50 |
| 4,824,601 | 4/1989 | Franklin | 252/401 |
| 5,097,041 | 3/1992 | Higel, et al. | 548/257 |

OTHER PUBLICATIONS

Kirk–Othmer, Encyclopedia of Chemical Tech., vol. 2, pp. 329–337, 3rd ed., 1978.
Fieser & Fieser, John Wiley & Sons, Reagent for Organic Synthesis, vol. 1., p. 1281, 1967.
Kirk–Othmer, Encyclopedia of Chemical Techn., vol. 1, 3rd ed., p. 532, 1978.
Chem. Abstracts, vol. 117 (1992) p. 649.

*Primary Examiner*—Richard L. Raymond
*Attorney, Agent, or Firm*—Mary Ann Tucker; Nestor W. Shust; Samuel B. Laferty

[57] ABSTRACT

Disclosed is a method for decolorizing alkylated diarylamines, which have been made using aluminum chloride catalyst, by mixing and optionally heating the colored diarylamine with clay, then separating the decolorized diarylamine from the clay. Alternatively, the alkylated diarylamines, which have been made using aluminum chloride catalyst, may be decolorized by passing the diarylamines through a filter medium comprising clay.

16 Claims, No Drawings

DECOLORIZATION OF ALKYLATED DIARYLAMINES

CROSS REFERENCE

This application is a continuation-in-part application of U.S. Ser. No. 07/993,924, filed Dec. 18, 1992, now abandoned.

FIELD OF INVENTION

The present invention relates to a method of decolorizing alkylated diarylamine antioxidants, made using aluminum halide catalyst, by treating the diarylamine with clay.

BACKGROUND

Alkylated diarylamines are known antioxidant compositions used as stabilizers in organic materials. Typically, these alkylated diarylamines are made by reacting an olefinic compound with diphenylamine in the presence of aluminum chloride catalyst. The resulting compounds are deeply colored, possibly due to strong activity of the catalyst or a reaction between the amine and the chloride. Such colored products have less appeal in the industry because certain antioxidant utilities require a high degree of purity or absence of colored contaminants, or simply because dark colored antioxidants are aesthetically less appealing.

Distillation may improve the color but often it is not enough since coloration reoccurs through oxidation of remaining contaminants. Therefore, it is desirable to find an adsorbent which can specifically remove the color contaminants generated from aluminum halide catalyst alkylation of diarylamines. Heretofore, decolorization of various amines required special adsorbents such as zinc, as disclosed in *Reagents for Organic Synthesis*, Vol. 1, p. 1281, Fiester & Fiester, 1967, bromine as disclosed in Derwent Abstract 117:25931b, page 649, Vol. 117, 1992, or ion-exchange resins, as disclosed in U.S. Pat. No. 5,097,041. Carbons, molecular sieves and silica gel which are common adsorbents for color contaminants as taught by Kirk-Othmer, *Encyclopedia of Chemical Technology*, 3rd ed., Vol. 1, p. 532 (1978), do not work well at all. Clays are known decolorizers for vegetable, animal and petroleum oils, but are not known for amines. U.S. Pat. No. 4,824,601 discloses the use of activated earth catalysts to produce alkylated diphenylamine liquid antioxidant compositions lighter in color than those obtained using aluminum chloride catalyst. Additionally, to achieve bleaching and alkylation using clay catalyst, the reaction must occur at a relatively high temperature, 160° C. or higher, which is not practical. Also, clay is a substantially less effective catalyst than aluminum chloride in that under equal conditions, substantially less diphenylamine is converted into product by clay as compared to aluminum chloride. This is demonstrated in Example 2 following herein. Therefore, it is more desirable to produce the alkylated diphenylamines using aluminum chloride catalyst. A new method of removing the color contaminants produced specifically from aluminum halide catalyzed alkylation of diarylamines has been discovered. The instant inventive method will enable the industry to utilize efficiently produced diarylamine antioxidant and subsequently decolorize it by a simple, efficient method of mixing and heating clay with the colorized antioxidants.

SUMMARY OF THE INVENTION

The inventive method is one for decolorizing alkylated diarylamines by mixing the colored alkylated diarylamine with clay, optionally heating the mixture, then separating the clay from the decolorized alkylated diarylamine.

DETAILED DESCRIPTION OF THE INVENTION

The present invention provides a method for decolorizing alkylated diarylamines, said method comprising; (a) mixing a colored alkylated diarylamine with clay to produce a mixture; (b) heating said mixture; and (c) separating said clay from said alkylated diarylamine. Any colored alkylated diarylamine can be decolorized by the present method. Diarylamines are known in the art and art described in Volume 2, pages 329-337 of Kirk-Othmer, *Encyclopedia of Chemical Technology*, 3rd ed., 1978, which is incorporated herein by reference. One skilled in the art, however, will appreciate that colored alkylated diarylamines requiring decolorization typically will be those made using aluminum halide catalyst, namely aluminum chloride. Suitable alkylated diarylamines include, but are not limited to those from diphenylamines; N-phenyl-naphthylamines; and phenothiazines, etc. For example, suitable alkylated diphenylamines include those having the following general formula:

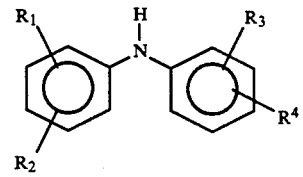

wherein
$R_1$, $R_2$, $R_3$ and $R_4$ independently are H, branched, or straight-chain $C_1$–$C_{12}$ alkyl radicals, benzyl group or a straight chain $C_1$–$C_4$ alkyl benzyl group.

Accordingly, suitable diphenylamines include but are not limited to, p,p'-dioctyl-diphenylamine; p,p'-dinonyl diphenylamine; p,p'-di-α-methylbenzyl diphenylamine; o,o'-diethyl-p,p'-dinonyldiphenylamine; and o,o'-diethyl-p,p'-di-α-methyl-benzyl diphenylamine. Those skilled in the art will appreciate that the diarylamine may consist of a physical blend of more than one diarylamine, such as one comprising a blend of p,p'-di(-butyl and/or octyl) diphenylamine; p-(butyl or octyl diphenylamine; p-tert-butyl-p'-tert-octyl-diphenylamine and diphenylamine or the blend from the reaction of diphenylamine and a mixture of diisobutylene and styrene.

Also included are derivatized alkylated diarylamines obtained from further reaction, such as the ones taught by U.S. Pat. No. 5,634,248 from the reaction of alkylated diarylamine, with aldehyde, or the ones taught by U.S. Pat. Nos. 3,509,214 and 3,573,206 from the oxidation of diarylamines, or the one taught by U.S. Pat. No. 3,492,233 from the dehydrocondensation of diarylamines and a lubricant, or the ones taught by U.S. Pat. No. 3,539,515 regarding peroxide-treated phenothiazines as an antioxidant, all of which are incorporated herein by reference.

Any clay, most of which are aluminosilicates, having decolorizing capacity is suitable. Conventional clays used for decolorization of mineral, vegetable and animal oils are suitable in the present inventive method. This includes a wide range of clay materials from fine-grained silts to clays composed of almost pure clay minerals. Crude clay, also known as Fuller's earth, is suitable. The preferred clays are those which have been acid treated, such as Fulcat ® sulfuric acid-activated Fuller's earth, commercially available from Laporte Industries. A particular suitable clay is bentonite acid-bleached clay known as Filtrol TM or Retrol TM grade clay. It is approximately 97% by weight aluminum silicate and approximately 1-3% crystalline silica. It is commercially available from Englehard Corporation, Jackson, Mississippi, U.S.A. as product Grade F-6 or Grade F-13. Other suitable clays will include montmorillonite, halloysite, and sepiolite and those composed of attapulgite.

In the method of the present invention, the alkylated diarylamine is mixed with the clay using conventional means for a sufficient time to allow for decolorization of the diarylamine. Typically, between 5-45 minutes mixing time is sufficient. Typically, the mixture will be thick and therefore heating the mixture will be advantageous. Best results are obtained when the mixture is heated to at least about 50° C. Although it is suitable to heat the mixture beyond 150° C., one skilled in the art will appreciate that it is more efficient to keep the temperature below 150° C. Desirably, the temperature at which the mixture is mixed will be from about 70° C. to about 150° C., preferably between about 80° C. to about 130° C., and most desirably between about 90° C. to about 120° C. and optionally to 150° C. The amount of clay necessary to decolorize the diarylamine is not critical although at least 0.5 % by weight, based on the total weight of the diarylamine desirably will be used. Generally, the more clay used, the better the results achieved. A Suitable range is between about 2% and 10% clay. The decolorized antioxidant alkylated diarylamine can be separated from the clay using any conventional method, especially filtration and preferably while the mixture is hot.

A further method of decolorizing diarylamines is by contacting of the diarylamine with clay surfaces, allowing the colored species to be associated as by absorption or adsorption (i.e. sorbed) by the clay and physically separating (as by filtration or otherwise isolating) the less colored diarylamines from the clay combined with the sorbed colored species. One way to contact the clay with the diarylamines is to form a packed column with the clay or use the clay as part of a filter media or filter bed. This method makes use of the fine particle size and high surface area of the available clay products. The temperature of the clay and/or the diarylamine may be increased above ambient as described above to decrease the viscosity of the diarylamine allowing shorter filtration times or higher throughput. The throughput of diarylamine may also be increased by using an apparatus capable of being pressurized on the input side of the filter or capable of maintaining below atmospheric pressure on the output side of the filter. Other methods of achieving high surface contact between solids and liquids may also be used with appropriate adjustments for the physical characteristics of the diarylamines and the available clay-based products. These may include things such as fluidized beds or the use of clay supported on an inert support medium or structure.

The colored alkylated diarylamine may be one which has been already treated by another means of decolorizing such as distillation. If the equipment for decolorization can handle the alkylated diarylamine at ambient temperatures (i.e., 20-30° C.) then heating is not a necessary step.

SPECIFIC EMBODIMENTS(S)

The following nonlimiting examples will provide the reader with a more detailed understanding of the invention.

EXAMPLE 1

A liquid antioxidant consisting of p,p'-di(butyl/octyl) diphenylamine; p-(butyl/octyl) diphenylamine; p-tert-butyl-p'-tert-octyl-diphenylamine; and diphenylamine was placed in a flask. Retrol TM, a clay from Mississippi was added in the amount of about 10% of the weight of the antioxidant. They were mixed and stirred at 120° C. for 30 minutes, then filtered while hot through a fritted funnel. The decolorized oil had a reading of <0.5-1.0 on the Fisher Scientific ASTM D1500 Colorimeter compared to a number >8 before the process. Use of carbons, silica gel or molecular sieves gave a color measurement of between 3.5-6.

EXAMPLE 2

To show the $AlCl_3$ is a much stronger catalyst than clay, 1 mole diphenylamine and 3 mole diisobutylene with 4% $AlCl_3$ (based upon the weight of diphenylamine) were refluxed at 105-110° C. for two hours, 85% of the diphenylamine was converted into a mixture 3:2 mono- and di-octylated diphenylamine. While under the same condition, the 4% $AlCl_3$ was replaced by 4% Retrol TM and only <5% of the diphenylamine was converted to mono-octylated diphenylamine.

EXAMPLE 3

The same blend of alkylated diphenylamines as in Example 1 was treated with 5% Retrol TM at 100° C. for 15 minutes, followed by distillation at 5mm Hg vacuum to afford a light-colored oil with a color reading of <0.5.

EXAMPLE 4

A distilled blend of alkylated diphenylamines made from an aluminum chloride catalyzed reaction of diphenylamine and a mixture of diisobutylene and styrene was decolorized by 5% Filtrol TM at 110° C. for 10 minutes. The color went from >8 to 1-1. 5.

EXAMPLE 5

A 200 grams of undistilled blend of the same alkylated diphenylamines as described in Example 4 was warmed to 160° C. and passed through a 5 gram bed of Filtrol TM grade 20 packed in a 150 ml fritted Buchner funnel with pores sizes of 40-60 microns. A water aspirator was used to supply vacuum to the receiver side of the Buchner funnel. The color dropped from >8 to 3.

EXAMPLE 6

A crude product of aluminum catalyzed reaction of diphenylamine an a mixture of diisobutylene and styrene was passed through the medium of Example 5. The crude product was the same crude product that was first distilled in Example 4 and contained some residual diphenylamine, diisobutylene, and styrene. Then the filtrate was distilled. The final color was between 3 and 3.5.

EXAMPLE 7

The same blend of alkylated diphenylamines as in Example 1 was passed through a chromatograph column packed with 5% Filtrol TM grade 6. The color went from >8 to 2.5.

Although the invention has been described in terms of specific embodiments of a manner, the invention may be practiced, this is by way of illustration only and the invention is not necessarily limited thereto since alternative embodiments and operating techniques will become apparent to those skilled in the art. Accordingly, modifications are contemplated which can be made without departing from the spirit of the described invention.

What is claimed is:

1. A method for decolorizing alkylated diarylamines, said method comprising:
   (a) mixing one or more alkylated diarylamines with clay to produce a mixture, said alkylated diarylamines having colored contaminants from the alkylation reaction of diarylamines with an aluminum halide catalyst;
   (b) heating said mixture, and
   (c) separating said clay from said alkylated diarylamine.

2. The method of claim wherein said alkylated diarylamines are alkylated diphenylamines.

3. The method of claim 1, wherein said alkylated diarylamines are a physical blend of p,p'-di(butyl and/or octyl) diphenylamine, p-(butyl or octyl) diphenylamine, p-tert-butyl-p'tert-octyl-diphenylamine and diphenylamine.

4. The method of claim 3, wherein said clay is acid treated clay.

5. The method of claim 4, wherein said heating is at a temperature of from about 90° C. to about 150° C.

6. The method of claim 5, wherein the amount of clay present is at least 0.5% by weight of the total amount of diphenylamine.

7. The method of claim 2, wherein the alkylated diphenylamines are p,p'-dioctyl-diphenylamine.

8. The method of claim 1, wherein said alkylated diarylamines are the reaction product of styrene, diisobutylene, and diphenylamine in the presence of an aluminum chloride catalyst.

9. A method for decolorizing alkylated diarylamines, said method comprising:
   a) contacting one or more alkylated diarylamines with clay surfaces, said alkylated diarylamines being the reaction product of olefinic compounds and diarylamines in the presence of aluminum chloride and having colored contaminants;
   b) allowing said colored contaminants to associate with said clay surfaces; and
   c) separating said alkylated diarylamines from said clay surfaces.

10. The method of claim 9, wherein said alkylated diarylamines are alkylated diphenylamines.

11. The method of claim 10, wherein said alkylated diphenylamines are a physical blend of p,p'-di(butyl and/or octyl) diphenylamine; p-(butyl or octyl) diphenylamine, p-tert-butyl-p'-tert-octyl-diphenylamine, and diphenylamine.

12. The method of claim 10, wherein said clay surfaces are surfaces of an acid treated clay.

13. The method of claim 11, wherein said clay surfaces are surfaces of an acid treated clay.

14. The method of claim 13, wherein the contacting step is conducted at a temperature from about 90 to about 150° C.

15. The method of claim 10, wherein the alkylated diphenylamines are p,p'-dioctyl-diphenylamine.

16. The method of claim 9, wherein said alkylated diarylamines are the reaction product of styrene, diisobutylene, and diphenylamine in the presence of an aluminum chloride catalyst.

* * * * *